United States Patent [19]
Walters

[11] Patent Number: 4,583,241
[45] Date of Patent: Apr. 15, 1986

[54] X-RAY TOMOGRAPHIC APPARATUS
[75] Inventor: Ronald G. Walters, Aurora, Ohio
[73] Assignee: Technicare Corporation, Solon, Ohio
[21] Appl. No.: 159,618
[22] Filed: Jun. 16, 1980

Related U.S. Application Data
[63] Continuation of Ser. No. 838,084, Sep. 30, 1977.

[51] Int. Cl.$^4$ ............................................. G01N 23/00
[52] U.S. Cl. ...................................... 378/19; 378/901
[58] Field of Search .................................. 378/19, 901

[56] References Cited
U.S. PATENT DOCUMENTS

| | | | |
|---|---|---|---|
| 4,101,768 | 7/1978 | Lill | 250/445 T |
| 4,149,247 | 4/1979 | Pavkovich | 378/901 |
| 4,398,251 | 9/1983 | LeMay | 378/901 |

*Primary Examiner*—Church, Craig E.

[57] ABSTRACT

The invention relates to a method for processing attenuation data to produce a tomographic image which requires only that each point within the scan circle be viewed from 180° in order to produce a full set of data. Data from views beyond 180° are redundant and do not improve the picture quality. The invention further relates to an X-ray source and detector arrangement in which the X-ray source is a fan-shaped beam of X-rays and the detectors are arranged about the scan circle for 180° plus approximately the angle of the fan beam. The invention further relates to method and apparatus for back projecting data from a polar coordinate system into a rectangular coordinate system in which the matrix points in the rectangular coordinate system can be loaded sequentially with the appropriate density value from the data line expressed in the polar coordinate system.

2 Claims, 10 Drawing Figures

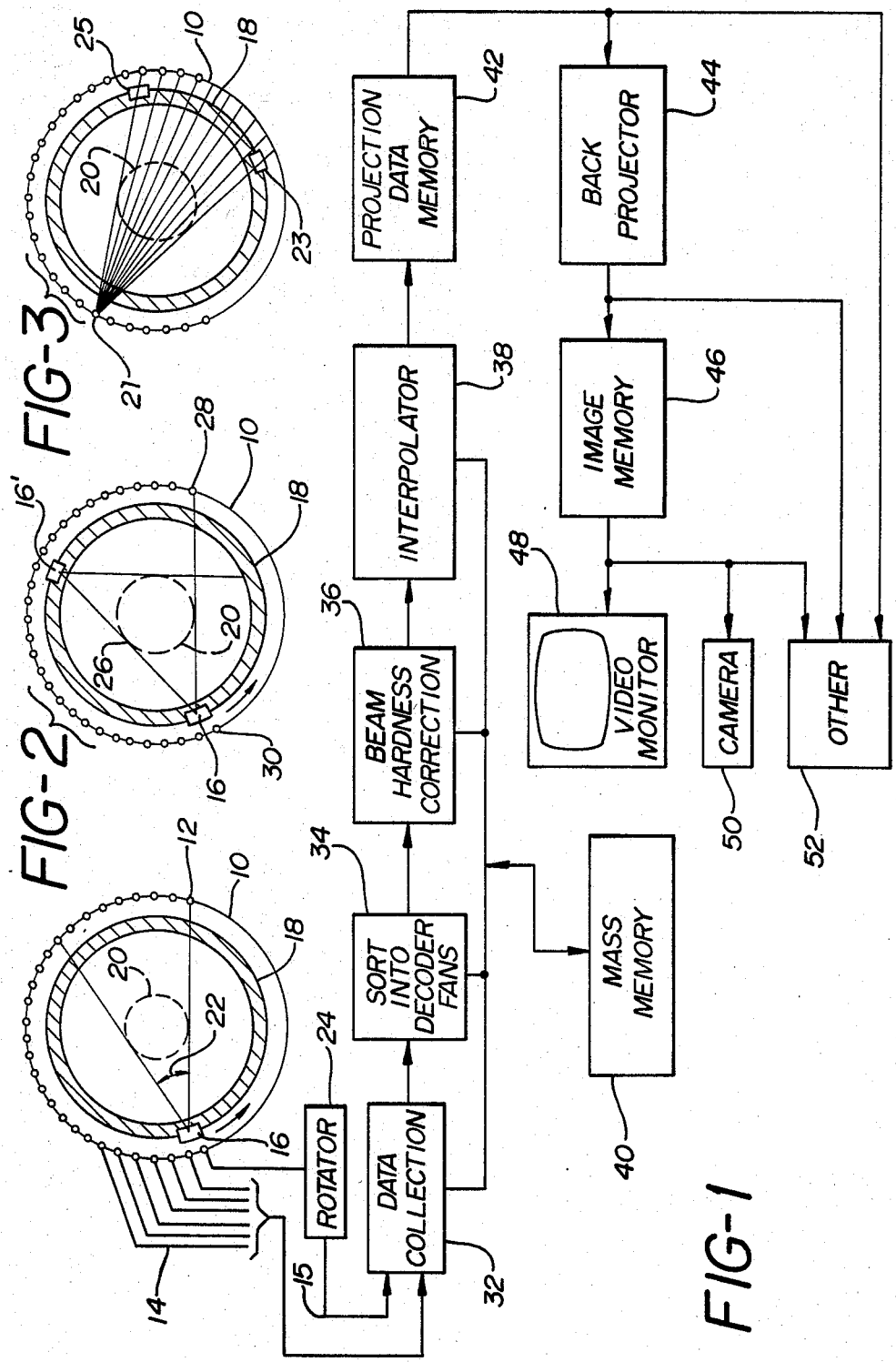

IMAGE COORDINATE SYSTEM

BACK PROJECTION COORDINATE SYSTEM

X-RAY TOMOGRAPHIC APPARATUS

This application is a continuation of application Ser. No. 838,084, filed Sept. 30, 1977.

BACKGROUND OF THE INVENTION

This invention relates to the method and apparatus for reconstructing objects and/or tomographic images from their projections. This invention has particular application in the field of medical computerized tomography.

There has been a constant trend towards faster and more accurate computerized tomographic scanners. The earliest medical scanners consisted of a source of radiation, such as X-rays, and a detector, the two of which traversed across the body to be examined in a linear manner, then were rotated a few degrees and the traverse repeated. In order to take sufficient readings to reconstruct a tomographic image, several minutes were required. For medical tomography, this length of time was undesirable because it meant holding the patient, and in particular the organ to be examined, totally still for this period of time. This allowed scans to be done on relatively stationary organs, such as the brain, but was not amenable to producing cross-sectional images of rapidly moving organs, such as the heart. Such a system is illustrated in U.S. Pat. No. 3,778,614.

In the quest of greater speed, it was found that a fan-shaped beam of radiation could be used which would irradiate a plurality of detectors simultaneously. See for example U.S. Pat. No. 3,881,110. With this setup, the traverse motion could be eliminated and the sole motion could be the rotation of the source and detectors. This system increased the speed but also increased the number of detectors—a very expensive component. Further different detectors took reading through different parts of the body. To sum these together, it was essential that each detector be equally sensitive and remain equally sensitive or else appear that more or less radiation was being absorbed by that part of the body.

The next step in increasing the speed was to have all the detectors stationary in a single rotating source (see U.S. patent application Ser. No. 726,556, filed Apr. 24, 1985, assigned to the U.S. Department of Health, Education and Welfare). Although this increased the speed, it required detectors to be placed 360° around the patient. Other variations of the stationary detector them have also been tried (see, for example, U.S. Pat. No. 4,031,395, the embodiment of FIG. 3 which has 360° stationary detectors, 360° of stationary X-ray tubes, and rotating collimator means). The geometry of this system is such that it is really a traverse and rotate system; but because detectors and X-ray tubes are stationary, it is able to function much more rapidly than the early moving detector and moving source traverse and rotate systems. But again, this system requires 360° of detectors. Indeed, as is pointed out on page 7 of the article *Reconstruction from Divergent Ray Data*, by A. V. Lakshaminarayanan in "Technical Report No. 92", State University of New York at Buffalo, Department of Computer Science, January, 1975, it was believed that 360° of views were required in any reconstruction system, such as those above, hence enough detectors to encircle the full 360° of the patient circle.

The present invention is a major breakthrough because it recognizes for the first time that 360° of views need not be taken in divergent fan beam geometry. Instead, the present invention recognizes that every point within the area to be examined need only be viewed from 180° of angles in order to produce a complete set of projection data. This, in turn, enables the system to operate much faster since the X-ray source need only scan a little over 180°, and it eliminates nearly half the detectors that would be needed in a 360° scan system.

The speed with which the patient was scanned was not the only concern with early computer tomographic devices for medical use. The earliest units were very slow in producing images and the images that they produced were not as sharp and clear as would be desired. The early traverse and rotate systems, in effect, took a series of density readings as they traversed and then filled sequential columns of a matrix with the sequential density readings. When the system rotated and traversed again, it would fill a second matrix. These matrices were then stacked, each rotated at their angle relative to the other, and the intensities at the corresponding point of each matrix, i.e. each vertical column of intensities, were summed. This was a slow system and less than accurate.

Then it was discovered that if such sum of intensities were at some degree modified by its surrounding intensities the image could be refined. However, these methods were even more time consuming, often requiring as much as fifteen minutes to transform the data into a tomographic image.

The next step towards speeding up the processing of data into images was to modify the intensity at each detector by the intensities read on the surrounding detectors before summing intensity values into the matrix. See, for example, U.S. Pat. No. 3,924,129. The system shown uses a number of geometrically derived approximations to make these modifications. Subsequently, a large number of articles have appeared which have used convolution theory to modify the intensity at each point as a function of its surrounding points. These all multiply the intensity data at a given point by a convolution function whose values are determined by the intensities read at surrounding points. The convolved intensity data is then stored in matrices for processing into an image representation. The convolution method is faster than the geometric method because functions are brought together as a unit rather than a series of individual point calculations. However, as pointed out above, it has heretofore been believed that the convolution interval need be from 0 to $2\pi$ radians, i.e. that absorption intensities must be read through all 360° around the circle surrounding the body. Again, the present invention will cut down the image processing time because it is only necessary to work with views which surround each point of the object to be viewed by 180°.

A further advantage of the present invention is that it includes a faster back projection system. The back projector works with data in the same order as the convolver, hence the back projector can back project the data into the image memory as it emerges from the convolver.

Another advantage of the present system is that each detector receives absorption data along paths passing through the entire body. Hence, if all detectors do not have precisely the same sensitivity, the differences will be averaged out without causing an error in the final tomographic image.

Another advantage of the present system is that it has a convolver function which provides a greater resolution, faster processing and simpler calculations all from fewer views.

SUMMARY OF THE INVENTION

The invention relates to an X-ray tomographic system which consists of an X-ray source which produces a fan beam of X-rays. The fan is wide enough to encompass the patient circle. The system further includes means for rotating the X-ray source at a constant rate about the patient circle for less than a full rotation. Further, there is a partial ring of detectors which surround the patient circle by 180° plus the angle of the detector fan beam plus the angle between adjacent detectors. In the preferred embodiment, this is about 215° for a patient circle of 50 cm. Attenuation data from the detectors is sorted into detector fans of attenuation data. This data then is processed including convolving it with a convolver function. The convolved data is then back projected into an image memory and displayed on a video monitor.

DESCRIPTION OF THE FIGURES

FIG. 1 is a block diagram of a system built in accordance with the present invention;

FIG. 2 illustrates the geometry of the detectors, the X-ray source and the fan beams;

FIG. 3 illustrates the detector fan for a random detector;

DESCRIPTION OF THE PREFERRED EMBODIMENT

Figure 4:
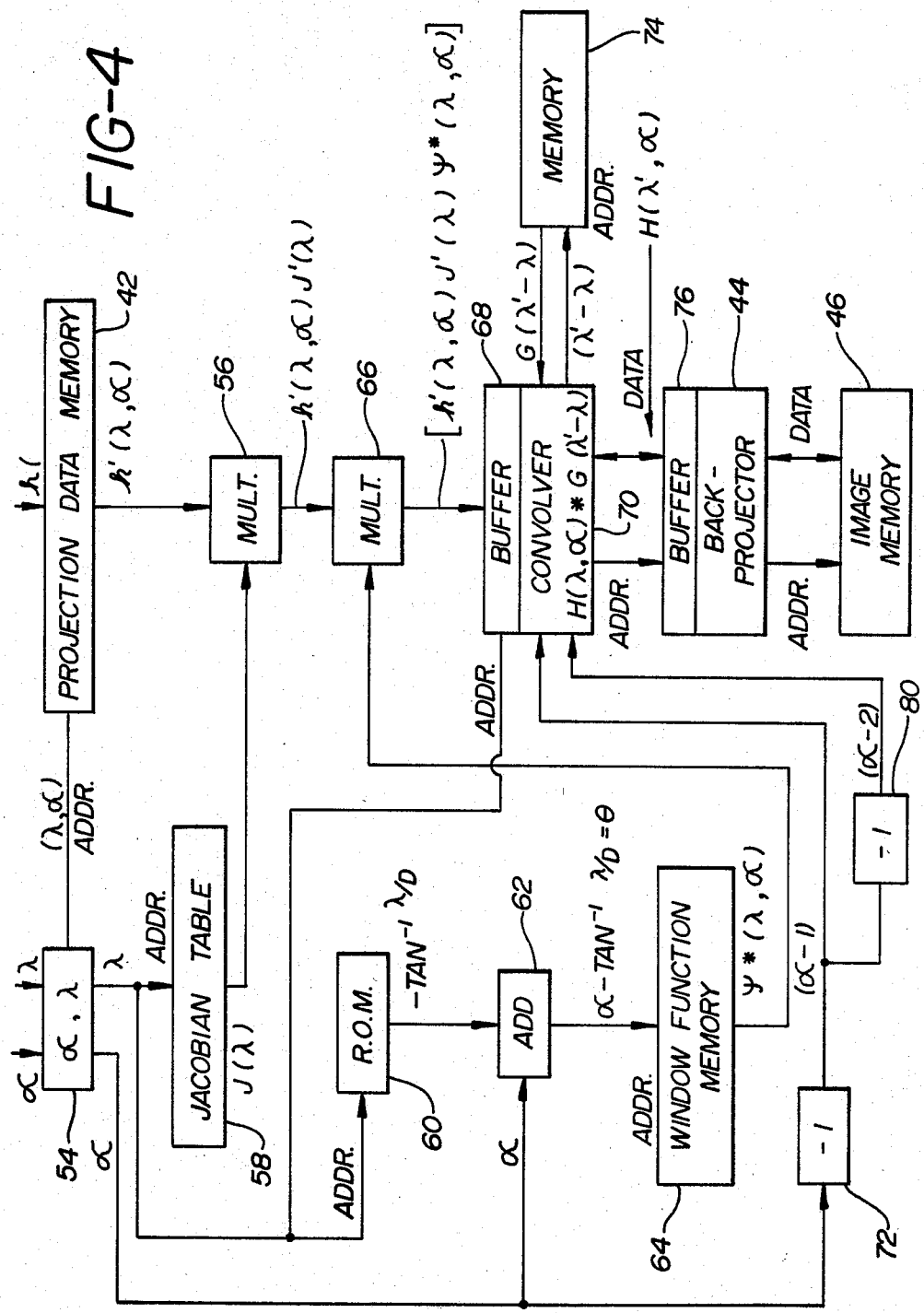
FIG. 4 is a block diagram of processing hardware built in accordance with the present invention for converting the projection data into convolved data and then projecting it into the image memory.

FIG. 1 shows a general physical setup of the apparatus. The apparatus for performing the actual physical examination consists of a stationary frame 10 upon which is mounted a series or array of X-ray detectors 12. These detectors may be individual scintillation crystals and photomultiplier tubes, or they may be the ends of light pipe which connect one or several detector stations to a single photomultiplier tube. Detectors 12 include means for converting the X-rays detected into an electrical signal indicative of the strength of the X-ray beam impinging upon the detector. Because the intensity of the X-rays was known at the source, the intensity of the X-rays impinging upon an individual detector is representative of the attenuation of the X-ray beam along the path between the source and the detector, i.e. the absorption by the components of the body located along that path. The electrical signal indicative of this intensity is fed from the individual detectors along electrical lines 14 to the processing equipment.

The apparatus further includes a single X-ray source 16 which produces a single fan-shaped beam or swath of X-rays. There is a means 24 for rotating the X-ray source at a constant rate around the patient or scan circle 20. Means 18 constrains the X-ray source to rotate along the arc segment of a circle's circumference. It will be noted that the detectors 12 are arranged only around a part of the circumference of the device. The X-ray source only rotates a similar number of degrees about the patient circle.

Looking to FIG. 2, the exact geometries of the device will become much clearer. The present invention has found that examining each point of the object being examined around an arc of 180° provides all the data to make a tomographic picture. Examining any given point for more than 180° only provides redundant data which must be removed. Accordingly, the geometry of the system should be such that the point 26 on the circumference of the patient circle is examined from all 180°, but no more. In order for this to happen, the X-ray source must move from its first position 16 counterclockwise around the patient circle to end position 16'. Similarly, only enough detector elements 12 need be provided to receive data around 180° of all points. It is readily apparent that the detectors need only extend from point 28 around the exterior of the device to point 30. Any detectors on a lower side of the circle between points 30 and 28 would produce redundant views which would only need to be filtered out before the signals could be processed. It will be seen that the exact number of degrees around the outer circumference which must be provided with detectors will vary the geometry of the system. It will vary with the relative diameters of the patient circle and the detector circle as well as the circle around which the X-ray source rotates. As the diameter of the patient circle approaches zero, the number of degrees around which detectors need be provided approaches 180°. It will further be seen that for a fan beam of X-rays which an angle 22 just sufficient to span the entire patient circle, that if the radius about which the X-ray source rotates is the same as the radius about which the detectors are located, then the detectors may be located around 180° of the circumference plus the angle 22 of the X-ray source. If the X-ray source rotates about a radius slightly smaller than the radius about which the detectors are arranged, then the number of degrees about which the detectors must be placed is just slightly less than 180° plus the angle of the source fan beam. Further, as a practical matter, the detectors are not a continuum but a series of discrete points. Thus, it may be necessary to rotate yet an additional angular amount equal to the angular spacing between detector elements in order to provide every point of the patient circle with at least 180° of views. If, for example, the detectors were spaced 4° apart, then if the X-ray source were rotated just far enough to subject point 26 to radiation from 180 different degrees, it is possible that because of the 4° spacing between detectors, data might only be received representing 176° of views about point 26.

Viewing the system from the point of view of one of the detectors 21, FIG. 3, it will be seen the detector 21 receives X-rays the entire time which X-ray source 16 is located between positions 23 and 25. However, with digital processing equipment, as the preferred embodiment uses, a continuum of intensity versus time is not readily processed. Accordingly, the amount of attenuation of the X-rays reaching detector 21 is measured periodically as the X-ray source traverses the arc between points 23 and 25, each sampling representing the attenuation along a path through the patient circle. The angular spacing of these paths determines the resolution of the final tomographic picture and may be as closely spaced as the physical limitations of the processing equipment will allow. Thus, although every detector is capable of producing a continuum of X-ray attenuation of data, the data processing equipment only takes a discrete number of X-ray attenuation readings at each detector.

Looking again to FIG. 1, wherein is further illustrated processing means connected to the detectors by lines 14 for processing a representation of the radiation attenuation in the patient circle and connected to means for displaying or storing the representation.

Each time the detectors are sampled, attenuation data from each detector that is irradiated is sent along one of lines 14 to the data collection means 32 where it digitizes the log of each detector's output. Each sampling, it will be apparent, represents attenuation data collected along one of the paths in the fan-shaped continuum of paths received by each detected element discussed above in reference to FIG. 3. A second signal along line 15 representative of the angular position of the X-ray source is also fed into data collector means 32 so that each attenuation reading is coordinated with the angle through the patient at which it was taken. The data as the log of the intensity is temporarily stored in mass memory 40 until at least one of the detector means has received all the attenuation data which it will receive. At this time, sort means 34 starts reorganizing the data into detector fan beams, that is, all the attenuation data taken by a single detector along all angles. The data is then corrected by beam hardness correction means 36 which averages several points at the end of each detector fan and subtracts the average from the entire fan thereby correcting the detector for gain drift. Following this, each data point is modified by a non-linear operator for beam hardness correction and fed into interpolator means 38. Means 38 interpolates the data into equal tangents (see equation No. 17 to follow) and feeds this information into projection data memory 42. This process is repeated until all detector fans have been processed. As described in greater detail in FIG. 4, as each detector fan is processed it is addressed into the reconstruction processing system 43 which adjusts the data for angular position, removes redundant data, and convolves the data with a convolver function. Back projector 44, along with image memory 46 transforms the the convolved data into a series of intensity representations for each point along each raster scan of the video monitor 48. Also connected to the image memory 46 may be a camera means 50, such as the camera marketed under the trade name of "Delta-Mat" by Ohio-Nuclear, Inc. of Solon, Ohio. Additionally, other storage or display means 52 may also be connected to the system at the user's option.

FIG. 4 is a block diagram of the reconstruction processing system. It will be noted that every beam path can be uniquely described by the angular position of the detector which detected it, and the angle within the detector fan which angle can also be expressed as a function of that angle such as its tangent. Means 54 receives two input signals, $\alpha$ which indicates the angular position of the detector and $\lambda$ which represents the tangent of the angle of the path within that detector's fan. The projection data h, that is the intensity or attenuation of the radiation along that beam path, is fed into projection data memory 42. A timing sequence T1 through T4 will more this data through the hardware. In the timing sequence, each successive value of $\lambda$ for a given $\alpha$ along with the corresponding projection data h is read in and processed until each $\lambda$ for a given fan has been processed through. At that time, the system moves on to the next detector, reads a new angle $\alpha$, and starts indexing the $\lambda$'s and h's through the system again. Projection data memory 42 contains the projection data indexed by angle $\alpha$ and $\lambda$ the tangent of the angle within the fan. Typically, this would be a RAM capable of storing all the fans, or in the case where data collection is slower than processing speed, a double buffer may be used. Means 54 addresses the $\alpha$ and $\lambda$ values being read to the projection data memory 42 which in turn feeds out the appropriate attenuation data $h'(\lambda,\alpha)$ to multiplier 56.

Memory 58 is pre-programmed with a Jacobian table and is addressed by $\lambda$. For each value of $\lambda$, there is a value stored within this table. For the mathematical function which is chosen for use in this particular preferred embodiment, the Jacobian equals $Cos^3(\arctan(\lambda/D))$, where D is the distance from the apex of the detector fan to center of the patient circle. Multiplier 56 multiplies projection data $h'(\lambda,\alpha)$ times the Jacobian obtained from the Jacobian table 58.

Read only memory 60 contains a table of arctangents. Read only memory 60 is addressed by each $\lambda$ and produces on its output a value equal to $-\arctan(\lambda/D)$. Adder 62 combines the angle $\alpha$ with the output of read only memory 60 to produce the sum which is $\alpha-\arctan\lambda/D$.

As indicated earlier, each point within the patient circle should be viewed from only 180°, no more. The redundant data would provide a surplus of values which would cause errors in the final tomographic projection. Accordingly, it is necessary to filter out the surplus values. From the geometry of the system, it is clear that certain values of $\alpha-\arctan\lambda/D$ will represent a redundant value, whereas others will not. Accordingly, a window function memory 64 is produces which provided a window function $\psi^*(\lambda,\alpha)$ which may be written as:

$$\psi^*(\lambda,\alpha) = \int_{-F}^{\pi + F} \psi(\lambda,\beta)\Lambda(\alpha,\beta)d\beta$$

where $$\psi(\lambda,\beta) = 1 \text{ if } 0 \leq \beta-\arctan\frac{\lambda}{D} \leq \pi$$

$$= 0 \text{ otherwise}$$

See the discussion surrounding equation 24 to follow. $\beta$ is the angular displacement about the body as is $\alpha$, however, $\beta$ can take a continuum of values whereas $\alpha$ can only take the discrete values corresponding to detector positions. An example of an interpolation function $\Lambda(\alpha,\beta)$ which could be used is:

$$\frac{\sin(\pi(a,\beta)/b)}{\pi(a,\beta)/b}$$

where b is the spacing between views i.e. spacing between adjacent detectors. Thus, all the values of the equation are known, and according with the predetermined program for each value of α-arctan λ/D a value of ψ*(λ,α) is produced.

The window function of ψ* goes to multiplier 66 where the output of multiplier 56 is multiplied by the window function to produce the product of the projection data times the Jacobian times the window function, i.e. h'(λ,α)J(λ)ψ*(λ,α). For simplicity, this product will be referred to as H (λ,α).

Buffer 68, as indicated above, is optional and need not be used unless the data collection speed is slower than the processing speed. Convolver 70 is a conventional convolver whose input may be double buffered by buffer 68 to allow overlapped convolution and back projection. Adder 72 changes the angle α to (α−1), i.e. indexes the α to the angle of the preceding detection fan. Buffer 68 is addressed by λ and convolver 70 receives the input indicative of (α−1). Memory 74 contains a table of values for a filter function called G (λ'−λ) which is addressed by convolver 70 for different values of (λ'−λ) to provide an output function G (λ'−λ) which is convolved to convolver 70 with function H (λ,α).

The value of H(λ,α) for specific values of λ and α is convolved with a convolving function G(λ'−λ):

$$H(\lambda',\alpha) = H(\lambda,\alpha) * G(\lambda'-\lambda)$$

That is, for a data line that is sampled periodically, the convolved data at the Mth sampled position on a data line α is:

$$H(M,\alpha) = \sum_{N=-\rho^*}^{\rho^*} H'(N,\alpha) * G(M-N).$$

A wide choice of filter functions may be used such as the one shown by Lakshminarayanan, supra in which $$G(M - N) = 1 \text{ when } M - N = 0$$
$$= \frac{4}{\pi^2(M-N)^2} \text{ when } M - N \text{ is odd}$$
$$= 0 \text{ when } M - N \text{ is even}$$

Other filter functions such as shown in U.S. Pat. No. 3,924,129 could be used instead.

The data from convolver 70 is addressed and fed into buffer 76, which is used in conjunction with back projector 78. The workings of the back projector will be further explained in conjunction with FIGS. 5 and 6.

There are several ways in which the back projection operation may be accomplished, see for example U.S. Pat. No. 3,924,129. The most desirable techniques, however, are those resulting in pixel driven algorithms, i.e. algorithms in which the matrix element location is the indpendent variable. The process herein not only uses such as algorithm, but also does not require tangent calculations. The present invention develops a simple set of linear relationships between the detector fan data and image matrix which permits the back projection to be described by a set of differential equations which may be implemented with a minimal amount of calculation. Minimizing the amount of calculation is very important because back projection requires on the order of the number of projection lines cubed of iterations and is generally the most time consuming part of reconstruction. Referring now to the mathematical derivation section to follow, it will be seen that the following is a description of the reconstruction process:

$$f(r,\phi) = \frac{D^2}{4a} \sum_{\alpha=-\infty}^{\infty} \sum_{\lambda=-\rho^*}^{\rho^*} h'(\lambda,\alpha)\cos\left(\arctan\frac{\lambda}{D}\right)\frac{1}{(\kappa\cos\mu)^2} G(\lambda'-\lambda)\psi^*(\lambda,\alpha)$$

Because one over (κ cos μ)² is a function only of R, φ, and α, it can be brought out of the inner summation. Accordingly, the equation can be rewritten as follows, where the inner summation has already been accomplished in convolver 70:

$$f(r,\phi) \frac{D^2}{4a} \sum_{\alpha=(F+A)}^{\pi+F+A} \frac{1}{(\kappa\cos\mu)^2} \sum_{\lambda=-\rho^*}^{\rho^*} h'(\lambda,\alpha)\cos(\arctan\lambda/D)G(\lambda'-\lambda)\psi^*(\lambda,\alpha)$$

Figure 5A:
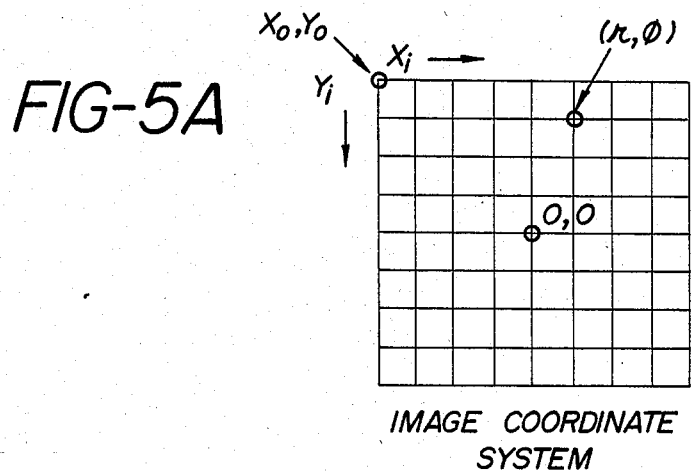
FIG. 5A illustrates the Cartesian coordinate system of the image memory.
Figure 5B:
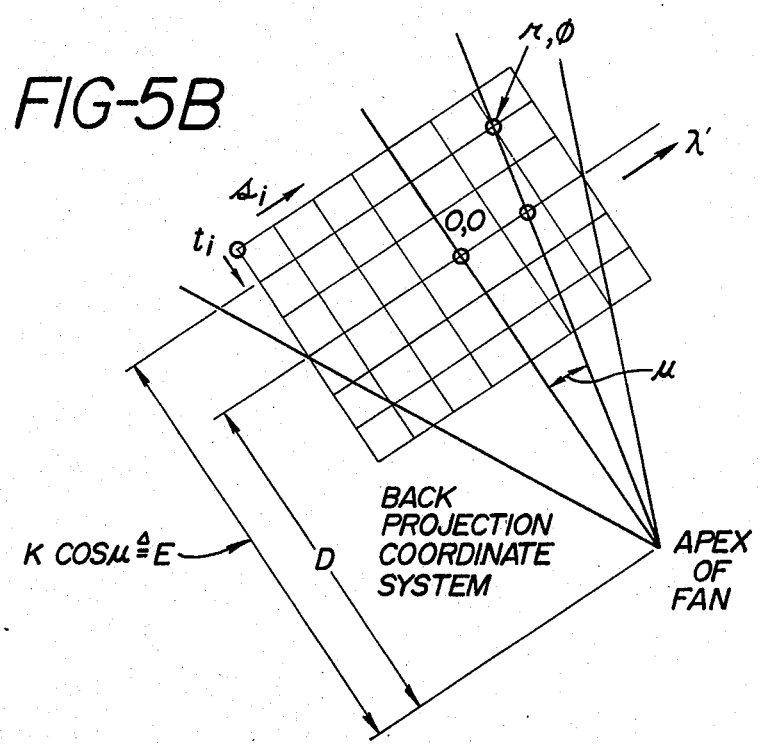
FIG. 5B illustrates a rotated Cartesian coordinate system for some selected fan beam.

FIGS. 5A and 5B show the relationship between the Cartesian image matrix and the geometry of FIG. 3. This relationship has been simplified in FIG. 5B by superimposing another Cartesian coordinate system (s,t) which is rotated into alignment with the divergent system. The description of κ(r,φ,α) and μ(r,φ,α) is simplified by transforming from the the (x,y) coordinate system to the (s,t) coordinate system. Using these systems in the relation shown in FIG. 5B, the above equation can be written in these variables as follows:

$$F(x,y) = \frac{D^2}{4a} \sum_{\alpha=-F-A}^{\pi+F+A} \frac{1}{E^2(x,y,\alpha)} H(\lambda',\alpha)$$

where $$E(x,y,\alpha) = D + x \sin\alpha + y \cos\alpha$$
$$\lambda' = (x\cos\alpha - y\sin\alpha)/E(x,y,\alpha)$$

where, of course, the above equations describe the operations to be performed by the back projector. It will be noticed that the system will work with traverse and rotate type scanning such as shown in U.S. Pat. No. 3,924,129 but is best suited to the fan beam type X-ray source.

The system must compute and index λ' into the convolved data H(λ',α), weighted by 1/E² and sum into the appropriate matrix point. It can be see that a simple linear relationship exists with the determination of E and λ'. In fact, the last two equations above. may be processed by finite differences in order to reduce the multiplications required.

For example, if one were to proceed through the matrix in the x direction, these two equations would become:

$$E_{J+1} = E_J + \frac{\partial t}{\partial x}$$
$$\lambda'_{J+1} = s_J + 1/E_{J+1}$$
$$s_{J+1} = s_J + \frac{\partial s}{\partial x}$$

where

-continued $$\frac{\partial s}{\partial x} = \sin \alpha; \frac{\partial}{\partial x} = \cos \alpha$$

Figure 6:
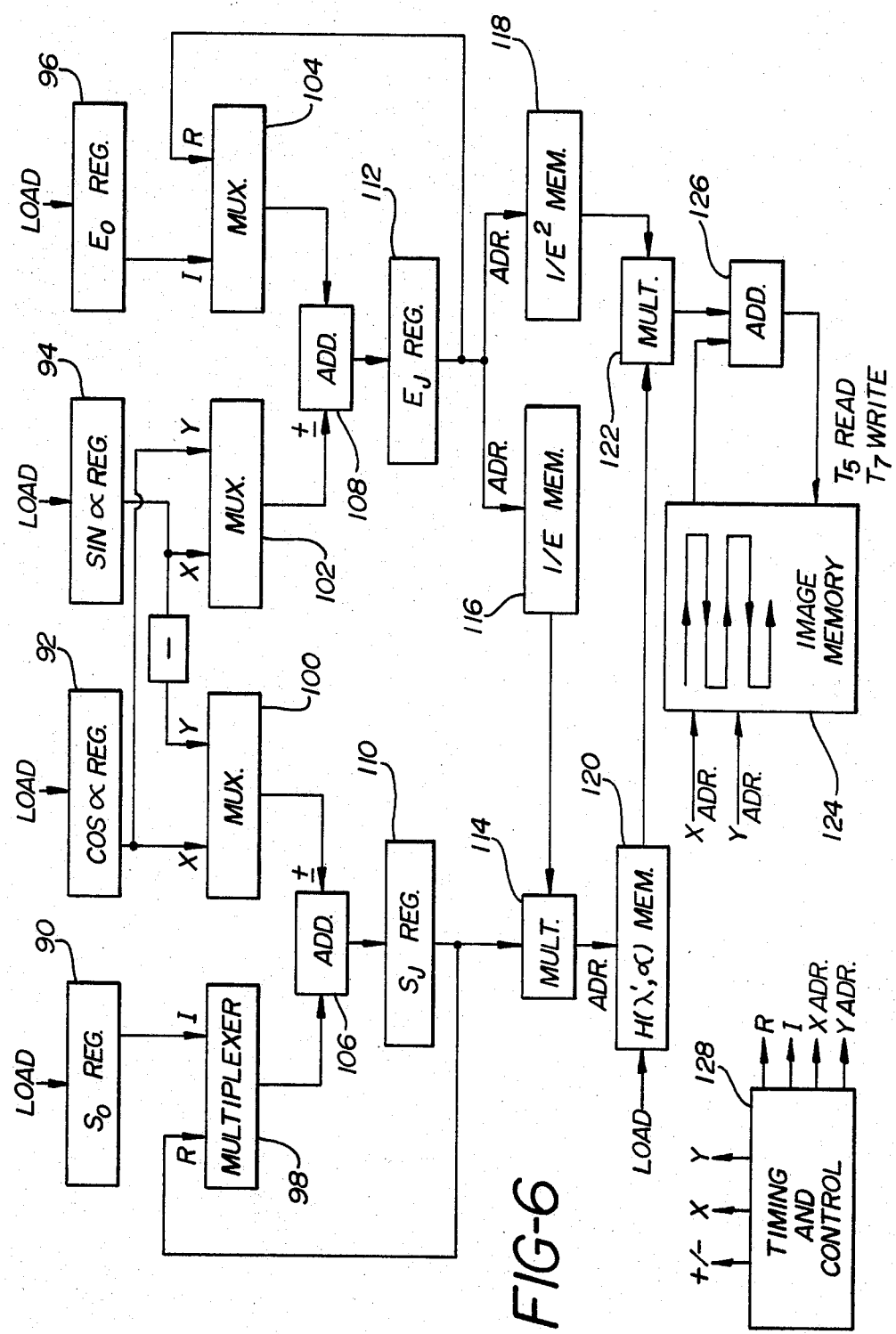
FIG. 6 is a block diagram of a back projection system built in accordance with the present invention.
Figure 7:
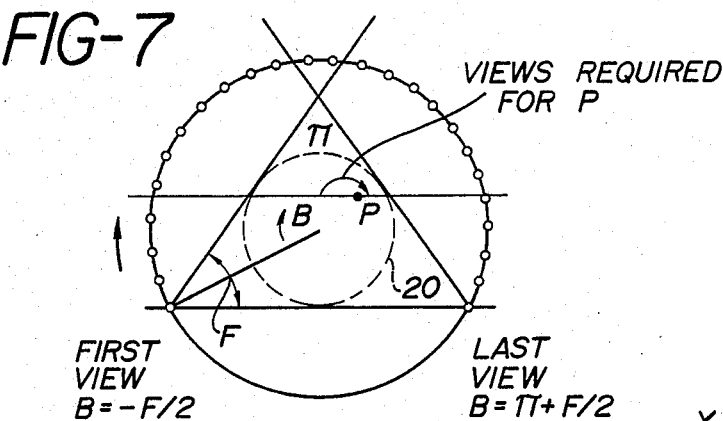
FIG. 7 illustrates the 180° plus ban beam geometry.

Similar equations would result proceeding through the matrix in the y direction. FIG. 6 is a block diagram of the back projector system. All the operations are shown as sequential, however, with the use of latches, the operations may be pipelined causing multiplies and memory accesses to be overlapped, significantly increasing the speed of these operations.

A host processor loads the value $\alpha$ describing the orientation of a single projection line into registers 92 and 94. The values $s_0$ and $E_0$ are determined by the computations above.

For each detector position, i.e. view angle $\alpha$, the multiplexers 98 and 104 are initialized with input I and $s_j$ register 110 and $E_j$ register 112 are cleared. In the run mode, the "R" input to multiplexers 98 and 104 is selected so that the $s_j$ register 110 and $E_j$ register 112 can be incremented. Timing and control means 128 initiates this incrementing each time it advances the address in the image memory by one position. The contents of the $s_j$ register 110 and the $E_j$ register 112 are incremented so that they progressively contain the value of $s_0$, $s_1$, $s_2$, etc. and $E_0$, $E_1$, $E_2$, etc. Memories 116 and 118 may be ROM or RAM memories. If RAM is used, the host processor could alter the geometry of the processor by loading different tables. These memories ae reciprocal tables for E and $E^2$. For each value of E, memory 116 puts out the value of one over E and memory 118 puts the value of one over $E^2$.

Multiplier 114 performs the multiplication set forth in the equation for $\lambda'$ above, i.e. forms the address $\lambda'$ into the projection data. Memory 120 is a RAM memory which contains the projection data $H(\lambda',\alpha)$ supplied by convolver 70 of FIG. 4. This projection data may be loaded into memory 120 from the convolver 70 directly or by a host processor.

As was the case in the processing equipment shown in FIG. 4, the back projector for given angle, $\alpha$, i.e. for a given detector position, processes each of the possible beam paths $\lambda$ within the view angle before going on to the next angle $\alpha$. Accordingly, the back projector need not wait until the convolver has processed data for all angles of $\alpha$ but need wait only to the end of the convolving of a specific angle $\alpha$ before making the back projection entries in image memory 46. For this given detector position $\alpha$, each time the memory 120 is addressed by $\lambda'$, the memory produces an output signal indicative of the convoluted data $H(\lambda',\alpha)$.

Multiplier 122 multiplies the output of memory 120 by the output of memory 118. This, in effect, weights the projection ray $H(\lambda',\alpha)$ by one over $E^2$, which is the value to be superimposed on the given matrix point. Adder 126 combines this value with the current contents of the matrix position. This process continues until all the projection data has been convoluted and back projected into the image memory. At this time, the contents of the image memory are effectively the tomograph of the cross section involved.

It is convenient for image memory 46 to have the same number of X lines as there are raster scan lines on a standard TV monitor, i.e. 512, and to have as many matrix points along each X line as there are data points along each raster scan of the standard TV monitor, i.e. 512. In this way, all that is necessary is a digital-to-analog converter and a standard TV monitor to transform the contents of the image memory into a video picture.

In some instances, it is desirable to interpolate the projection data during back projection. This can be done by addressing the two nearest points in the $H(\lambda',\alpha)$ memory 120 by obtaining addresses with fractional parts and using another adder and multiplier to form a linear interpolation at the output of the memory. This, however, can be costly in hardware and processing time. A more convenient way is to pre-interpolate $H(\lambda',\alpha)$ in the host processor which produces a longer data line then compute correspondingly high precision addresses into memory 120. Although this requires a larger memory, it has the computational advantage and interpolation is done once per view rather than approximately once per imager line per view.

In some cases, the back projector can be made many times faster than the generally large image memory, causing the processor to be input-output bound. This can be resolved by buffering several sets of projection data in fast memory and buffering one or more image memory lines in fast memory. In this way, several views can be projected into each image line before a transfer is made into the image memory. This increases the effective speed of the image memory by an amount proportional to the number of projection lines buffered.

The next section will describe the mathematics behind the convolution function used in the preferred embodiment. It will, of course, be understood that the equipment described in FIG. 4 can operate with other convolution functions although this might require changing the values in some of the tables in some of the memories, and the convolution function to be described can be used with other equipment. For example, a multipurpose digital computer or microprocessor could be used. Further, the back projection system can be used independently of the convolution function or the hardware of FIG. 4, and conversely other back projectors can be used with the hardware of FIG. 4 and/or the convolution function to be described in the following.

MATHEMATICAL DERIVATION

Figure 8:
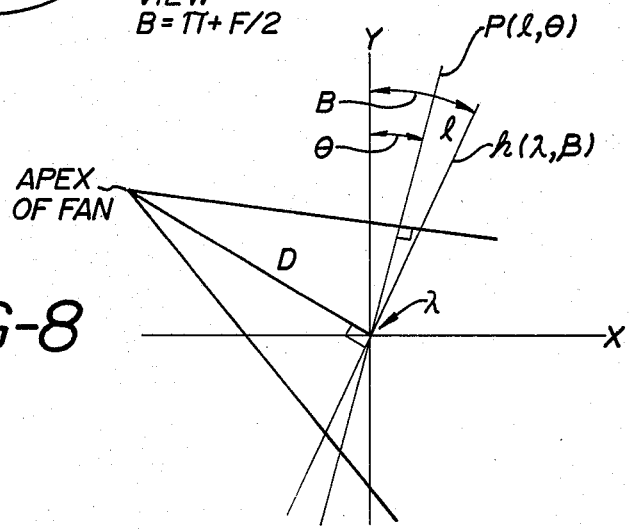
FIG. 8 is a geometric illustration showing a change in coordinates.

This mathematical derivation will view the system from the point of view of a detector element, such as detector 21 shown in FIG. 3. Now if a line $h(\lambda,\beta)$ were drawn, as is shown in FIG. 8, perpendicular to center ray of the fan, then all the lines of the fan would intersect that line. Each beam within the fan has a single value indicative of the attenuation along the beam path. If this value were applied to line h in FIG. 8 at the point at which each fan beam crossed it, then line h would have a series of amplitudes indicative of the attenuaton along the ray which crossed the line at that point. These individual discrete amplitudes can be interpolated into a smooth continuous function. In this manner then, line h can be said to be the data line for this fan view of the object examined. The value along any point on line h can be addressed by knowing the apex of the detector fan (i.e. detector position) which is defined by angle $\beta$ and the angle within the fan which is equivalent to defining a position along line h. Angle $\beta$ is related to angle $\alpha$, above, in that both describe the angular position of the apex of the detector fan detector position) with respect to the body, but unlike angle $\alpha$ which takes only discrete values corresponding to actual detector positions in the physical embodiment of the system, angle $\beta$ is a continuous function which takes any angular value.

Earlier tomographic systems employed a traverse and rotate system in which the detector viewed the attenuation along a set of parallel beam paths, then was rotated and viewed another set of parallel beam paths at some angle to the first set, etc. For any given object, projection data from the traverse and rotate system, is the same as the projection data from the rotating fan beam system. The individual data points will be different but the totality of the data will provide the same image. Where $p(l,\theta)$ is the projection data for traverse and rotate system, the relationship between the traverse and rotate system and rotating fan beam system can be expressed as $$p(l,\theta) = h(\lambda,\beta) \quad (1)$$

where, looking to FIG. 8, simple geometry shows the following relationships:

$$\theta = \beta + \tan^{-1}(\lambda/D) \quad (2)$$

$$l = \lambda \cos \tan^{-1}(\lambda/D) \quad (3)$$

thus, the projection data for the rotating fan beam system can also be expressed as:

$$h(\lambda,\beta) = p(\lambda \cos(\tan^{-1}(\lambda/D)), \beta + \tan^{-1}(\lambda/D)) \quad (4)$$

From the central section theorem, it is known that for a point to be reconstructed:

$$f(r,\phi) = \int_0^\pi \int_{-\infty}^\infty |R| F(R,\theta) \exp[2\pi i R r \cos(\theta - \phi)] dR d\theta \quad (5)$$

where, $f(r,\phi)$ is a two-dimensional image in real space which is to be reconstructed and wherein $r$ and $\phi$ are the polar coordinates for the points in real space and where $F(R,\theta)$ is a fourier transform where $R$ and $\theta$ are the polar coordinates in fourier space. It will be noted that the central section theorem is expressed with different limits that the limits shown in the article by A. V. Lakshminarayanan, supra. The proof, to follow, will show that it is only necessary to integrate from 0 to $\pi$ and not as Lakshminarayanan pointed out on page 7 of his article from 0 to $2\pi$. It is, of course, obvious that the integrals in polar coordinates from 0 to $2\pi$ for the angular displacement and zero to infinity for the radial displacement is the equivalent of integrating from 0 to $2\pi$ for the angular displacement and minus infinity to plus infinity for the radial displacement, since both sets of integrals sample all the same points.

The fourier transform of $f(r,\theta)$ is related to the projection by:

$$F(R,\theta) = \int_{-\rho}^{\rho} p(l,\theta) \exp(-2\pi i R l) dl \quad (6)$$

or inserting the relationships set forth in equations 2, 3, and 4 into equation 6, it can be rewritten:

$$F(R,\theta) = \int_{-\rho^*}^{\rho^*} h\left(\lambda, \theta - \tan^{-1}\frac{\lambda}{D}\right) \exp\left[-2\pi i R \lambda \cos\left(\tan^{-1}\frac{\lambda}{D}\right)\right] J(\lambda) d\lambda \quad (7)$$

where $\rho$ is the radius of the object examined in real space, $\rho^*$ is the equivalent of the radius of the object described in terms of $\lambda$ and $J(\lambda)$ in the Jacobian of the transformation, in this case and partial derivative of $l$ with respect to $\lambda$ where more precisely:

$$\rho = \lambda \cos(\tan^{-1} \rho^*/D) \quad (8a)$$

$$J(\lambda) = \cos^3(\tan^{-1}\lambda/D) \quad (8b)$$

As we indicated above, angle $\beta$ in the data line $h(\lambda,\beta)$ corresponds to the detector position and, because there are a discrete number of detectors, h is not continuous in $\beta$. Because $h(\lambda,\beta)$ will be sampled in $\beta$, a continuum in $\beta$ will be required. Thus, it will be necessary to interpolate h into a continuous function in $\beta$. This can be done by using an interpolation function $\Lambda$ which can be anyone of a number of interpolation functions. One example of an interpolation function which can be used is:

$$\Lambda(\alpha,\beta) = \frac{\sin[\pi(\alpha - \beta)/b]}{\pi(\alpha - \beta)/b} \quad (8c)$$

Thus, $h(\lambda,\beta)$, which is continuous in $\beta$, can be rewritten:

$$h(\lambda,\beta) = \int_{-J}^{\infty} h'(\lambda,\alpha) \Lambda(\alpha,\beta) \delta'(\alpha) d\alpha \quad (9)$$

where $\alpha$ is the discrete angles corresponding to the detector positions in the physical embodiment and $\beta$ is the continuum of angles corresponding to $\alpha$. Where $$\delta'(\alpha) = \text{Sampler}\left(\text{e.g. } \delta\left(\sin\left(\frac{\alpha\pi}{b}\right)\right)\right) \quad (9a)$$

$$b = \text{angular displacement between views} \quad (9b)$$

Other interpolators and samplers can, of course, be used provided only the compatability between them be maintained.

Introducing a fourier filter function $B(R,\theta)$ which takes the values one and zero, under the conditions as set forth below in conjunction with equation (14), substituting the equivalents found in equations 7 and 9 into equation 5, and changing the order of integration, equation 5 can be rewritten as:

$$f(r,\phi) = \int_{-\infty}^{\infty} \int_{-\rho^*}^{\rho^*} \Omega(R,\lambda) J(\lambda) \int_{-F}^{\pi+F} \psi(\lambda,\beta) \Phi(\alpha,\beta,\phi,r,R) \int_{-\infty}^{\infty} h'(\lambda,\alpha)\delta'(\alpha)\Lambda(\alpha,\beta) d\alpha d\beta d\lambda dR \quad (10)$$

where F is one-half the angle of the detector fan beam and:

$$\Omega(R,\lambda) = |R| \exp[-2\pi i R \lambda \cos(\tan^{-1}\lambda/D)] \quad (10a)$$

$$\Phi(\lambda,\beta,\phi,r,R) = \quad (10b)$$

-continued $$B(R, \beta + \tan^{-1}\lambda/D)\exp[2\pi i R r \cos[\beta + \tan^{-1}(\lambda/D) - \phi]$$

and where $\psi(\lambda,\beta)$ is a window function to cut out superfluous angular views defined by:

$$\psi(\lambda,\beta) = 1 \text{ if } -\tan^{-1}\lambda/D \leq \beta \leq \pi - \tan^{-1}\lambda/D \quad (11)$$
$$= 0 \text{ otherwise}$$

As was pointed out earlier, in order to view every point of the patient circle from at least 180°, it will occur that some points will be viewed from more than 180°. To prevent the superfluous attenuation readings from being used twice, thus giving erroneous sums to be used in computing the final tomographic image values, these extra views must be removed. Accordingly, this function sets to zero the attenuation data received along the superfluous beam paths and projected onto the data line. Now, because the redundant angular views have been removed by function $\psi$ and because h was made continuous in $\beta$ in equation 9, it is possible to change the variable of integration from $\theta$ to $\beta$. Changing the variable of integration in equation 10 from $\theta$ to $\beta$ and changing the order of integration, equation 10 can be rewritten:

$$f(r,\phi) = \int_{-\infty}^{\infty} \int_{-\rho^*}^{\rho^*} \Omega(R,\lambda)J(\lambda) \int_{-\infty}^{\infty} h(\lambda,\alpha)\delta'(\alpha) \int_{-F}^{\pi+F} \psi(\lambda,\beta)\Lambda(\alpha,\beta)\Phi(\lambda,\beta,\phi,r,R)d\beta d\alpha\, d\lambda\, dR \quad (12)$$

or by changing the order of integration once more:

$$f(r,\phi) = \int_{-\infty}^{\infty} \delta'(\alpha) \int_{-\rho^*}^{\rho^*} h'(\lambda,\alpha)J(\lambda) \int_{-F}^{\pi+F} \psi(\lambda,\beta)\Lambda(\alpha,\beta) \int_{-\infty}^{\infty} \Omega(R,\lambda)\Phi(\lambda,\beta,\phi,r,R)dR d\beta d\lambda\, d\alpha \quad (13)$$

Figure 9:
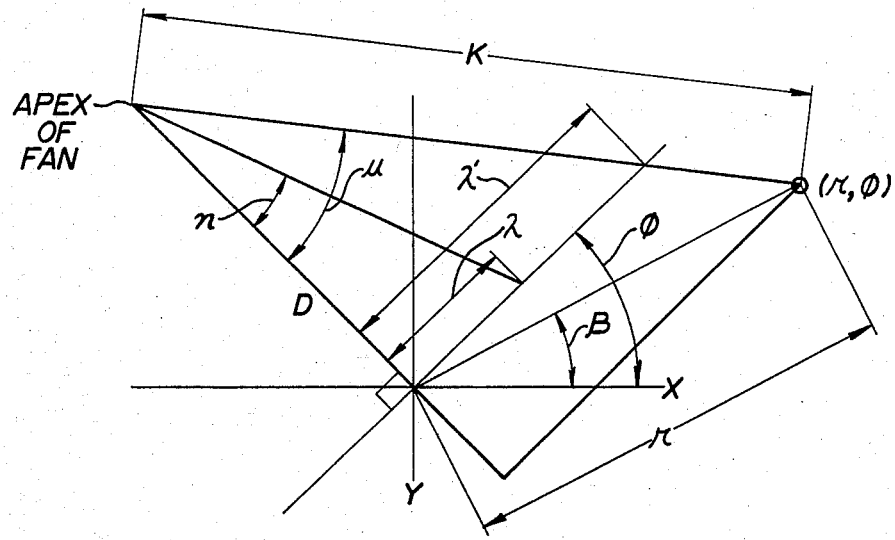
FIG. 9 is the geometry illustrating another change of coordinates.

In order to get a filter function that looks like a convolution function, it is helpful to change the coordinates such that each point within the patient circle will be defined by its distance from the apex of the fan and by the angle between center of the fan and a line which connects the apex with the point. This distance will be called $\kappa$ and the angle $\mu$. FIG. 9 illustrates the relationship between $(\kappa,\mu)$ and $(r,\phi)$. Introducing this change of coordinates, the filter function B can be rewritten:

$$B_{\lambda,\beta,r,\phi}(R,\theta) = 1 \text{ for } |R| \leq D/(2a\kappa\cos\mu\cos(\tan^{-1}\lambda/D)) \quad (14)$$
$$= 0 \text{ for } |R| > D/(2a\kappa\cos\mu\cos(\tan^{-1}\lambda/D))$$

If the sampling in $\lambda$ along the data line is to be done at intervals of a, where a is some positive constant, then it is equivalent to evaluate $h(\lambda,\beta)$ for values of $\lambda$ equal to Na. Defining the last integral of equation 13 as $g(\lambda'-\lambda)$ and substituting for $\mu$ and $\Phi$ in accord with equations 10a and 10b and, further, changing the limits of integration in accord with equation 14, then this last integral can be written as:

$$g(\lambda' - \lambda) = \int_{-\infty}^{\infty} \Omega(R,\lambda)\Phi(\lambda,\beta,\phi,r,R)dR = \quad (15)$$

$$\int_{-2a\kappa\cos\mu\cos\left(\tan^{-1}\frac{\lambda}{D}\right)}^{D/2a\kappa\cos\mu\cos\left(\tan^{-1}\frac{\lambda}{D}\right)} |R|\exp[2\pi i R\kappa\cos\mu(\lambda' - \lambda)\cos\frac{\left(\tan^{-1}\frac{\lambda}{D}\right)}{D}]d$$

this can be rewritten as:

$$g(\lambda' - \lambda) = \frac{D^2}{(\kappa\cos\mu)^2(\cos(\tan^{-1}\lambda/D))^2(\lambda' - \lambda)^2} \int_{-\frac{(\lambda'-\lambda)}{2a}}^{\frac{\lambda'-\lambda}{2a}} |I|\exp(2\pi i T)dI \quad (16)$$

where:

$$T = (\kappa/D)Rt \quad (16a)$$

$$t = (\lambda' - \lambda)\cos\mu\cos(\tan^{-1}\lambda/D) \quad (16b)$$

It is apparent that the integral of equation 16 can be evaluated. Thus, performing the integration and choosing $\lambda$ equal to Na, where a is the sampling integral and N is an integer, then:

$$g(M - N) = \frac{D^2 G(M - N)}{Ha(\kappa \cos \mu)^2 \left(\cos\left(\tan^{-1}\frac{Na}{D}\right)\right)^2} \quad (17)$$

where:

$$G(M - N) = 1 \text{ if } (M - N) = 0$$
$$= \frac{4}{\pi^2(M - N)^2} \text{ if } M - N \text{ is odd}$$
$$= 0 \text{ if } M - N \text{ is even}$$

where M is the projection being sampled and N is the total number of projections. Substituting $g(\lambda'-\lambda)$ into equation 13 and replacing the integrals with discrete summations, referring to FIG. 9, it can be seen that:

$$f(r,\phi) = \sum_{\alpha=-\infty}^{\infty} \sum_{\lambda=-\rho^*}^{\rho^*} h'(\lambda, \alpha)J(\lambda) \int_{-F}^{\pi+F} \psi(\lambda,\beta)\Lambda(\alpha,\beta)g(\lambda' - \lambda)d\beta \quad (19)$$

-continued $$\kappa(\beta,r,\phi) = [r\cos/\beta - \phi))^2 + (D + r\sin(\beta - \phi)^2]^{\frac{1}{2}} \quad (20)$$

$$\mu(\beta,r,\phi) = \tan^{-1}(r\cos(\beta - \phi)/(D + r\sin(\beta - \phi))) \quad (21)$$

In order to achieve a spatially invariant and hence computationally feasible convolution function, it is necessary that $g(\lambda'-\lambda)$ be removed from the integral. $g$, however, is the function of $(\beta,r,\phi)$. But note that interpolator $\Lambda(\alpha,\beta)$ is a very narrow function which weights $g(\lambda'-\lambda)$ very strongly for small values of $\alpha-\beta$. For systems with adequate view spacing, errors of less than 0.1% will arise from the following approximation:

$$g(\lambda' - \lambda,\beta,r,\phi) \approx g(\lambda' - \lambda,\alpha,r,\phi) \quad (22)$$

which is to say that if the detectors are close enough together g can be evaluated as a function of the discrete angle $\alpha$ which marks the position of discrete detectors rather than of the continuous angle $\beta$. Thus, g is always evaluated as of the nearest detector point in this approximation. This, however, allows g to be removed from the integral. With this approximation, equation 19 can be rewritten as follows:

$$f(r,\phi) = \frac{D^2}{4a} \sum_{-\infty}^{\infty} \sum_{-\rho^*}^{\rho^*} h'(\lambda, \alpha)\cos(\tan^{-1}\lambda/D) \frac{1}{(\kappa \cos \mu)^2} G(\lambda' - \lambda)\psi^*(\lambda,\alpha) \quad (23)$$

where by previous definition:

$$\psi^*(\lambda,\alpha) = \int_{-F}^{\pi + F} \psi(\lambda,\beta)\Lambda(\alpha,\beta)d\beta \quad (24)$$

$\psi^*$ is simply a convolution of the interpolator $\Lambda$ with the window function $\psi$. It may be applied as a weighting function on the projection data and because the kernel functions can be made stationary. $\psi^*$ need only be computed once and simply shifted to the appropriate position on the projection data as determined by $\alpha$. The summation limits on $\alpha$ from minus infinity to infinity are hard to evaluate. However, it is noted that because the interpolator is narrow, $\psi^*$ will remain substantially rectangular similar to $\psi$. If one were to choose some distance A from the point where $\psi$ goes to zero and in which $\psi^*$ is sufficiently close to zero, then the limits on equation 23 change from between minus infinity and infinity to between $-F-A$ and $\pi+F+A$. In practice, it has been found that excellent results have been obtained with A equal to zero; thus, equation 23 can be rewritten as follows:

$$f(r,\phi) = \frac{D^2}{4a^2} \sum_{\alpha=-F}^{\pi+F} \sum_{\lambda=-\rho^*}^{\rho^*} h' \frac{(\lambda,\alpha)\cos(\tan^{-1}\lambda/D)}{(\kappa \cos \mu)^2} G(\lambda' - \lambda)\psi^*(\lambda,\alpha) \quad (25)$$

where F is one-half the detector fan angle. Thus, the resulting algorithm is simply a convolution and back projection with the addition of a weighting function which is to be applied to the projection data prior to convolution.

CONCLUSION

It can, thus, be seen that with equation 25, the density for each point within the patient circle can be calculated. Thus, a two-dimensional density image f(r,φ) can be evaluated for all r and φ within the patient circle and a tomographic image obtained. The above system only needs enough detectors so that each point in the patient circle can be viewed from 180° in order to process the attenuation data into tomographic image. It will be readily apparent that other mathematical approximations can be made and other interpolation functions used to obtain the equation to be evaluated. This invention is not limited to a single interpolation function or approximation; instead, the above interpolation functions and approximations are by way of illustration only. Further, it will be appreciated that the processing and back projection hardware can take many forms in addition to the above-disclosed layout, for example, a digital computer.

I claim:

1. A method of producing a tomographic representation of a planar region of a patient disposed within a scan circle, the tomographic representation representing the radiation transmissive and absorptive properties of body tissues of the patient planar region in the scan circle, the method comprising:
    irradiating the scan circle with a fan-shaped swath of penetrating radiation, the fan-shaped swath of radiation being uniformly distributed over a source fan angle which spans the scan circle;
    rotating the source of penetrating radiation concentrically around the scan circle over an angle of 180° plus the source fan angle;
    at a plurality of discrete radiation detection points which are disposed concentrically around the scan circle, detecting penetrating radiation from the source which has traversed the scan circle, each discrete detection point receiving radiation from the source which has traversed the scan circle over a detector fan angle which spans the scan circle;
    converting the radiation received at detection points spanning 180° plus the detector fan angle into fan beam data lines each of which represents variations in the intensity of radiation traversing the scan circle and converging upon a corresponding detection point;
    convolving the fan beam data lines with a convolution function;
    back projecting the convolved fan beam data lines; and,
    converting the back projected, convolved fan beam data lines into said tomographic representation, whereby the fan beam data lines are processed into the tomographic representation without being sorted into parallel ray data sets.

2. A radiographic diagnostic apparatus for irradiating at least a planar region of a patient disposed within a scan circle with X or gamma radiation which is transmissible through the patient planar region along substantially straight lines and for producing a tomographic representation of the radiation transmission and absorption properties of the patient planar region, the apparatus comprising:
    a source of X or gamma radiation mounted for rotational movement along a first path defined by a circular arc segment which is concentric with the scan circle, said source of radiation generating a fan-shaped swath of radiation distributed over a source fan angle, which source fan angle spans the scan circle;

means for rotating said radiation source continuously along the first arc segment over an arc of substantially 180° plus said source fan angle;

a plurality of radiation detectors for receiving radiation and producing electric signals indicative of the intensity of radiation received, said plurality of detectors being stationarily mounted at regular center-to-center intervals along a detector arc segment of a second circular path which is concentric with the scan circle, each detector being disposed to receive radiation substantially continuously from the radiation source through the scan circle, there being a detector fan angle which is defined by the angle over which radiation passing from the radiation source through the scan circle is received by each detector, each radiation detector producing a continuum of electric signals to form a fan beam data line representing variations in the intensity of received radiation which has traversed the scan circle, whereby each fan beam data line represents the intensity of radiation converging on the corresponding detector along rays distributed over the detector fan angle as the source rotates behind the scan circle;

convolver means for convolving fan beam data lines from detectors spanning an arc of substantially 180° plus the detector fan angle with a convolution function;

back projecting means for back projecting the convolved fan beam data lines into an image memory; and, display means for transforming the data in the image memory into said tomographic representation.

* * * * *